United States Patent [19]
Beattie et al.

[11] Patent Number: 5,364,344
[45] Date of Patent: Nov. 15, 1994

[54] DUAL LUMEN CATHETER

[75] Inventors: David Beattie; John Miller; Victor Gamble, all of Salt Lake City, Utah

[73] Assignee: The Kendall Company, Mansfield, Mass.

[21] Appl. No.: 139,677

[22] Filed: Oct. 22, 1993

[51] Int. Cl.$^5$ .......................................... A61M 25/00
[52] U.S. Cl. ........................................ 604/43; 604/280
[58] Field of Search ................................ 604/43, 280

[56] References Cited

U.S. PATENT DOCUMENTS

| | | | |
|---|---|---|---|
| 4,406,656 | 9/1983 | Hattler et al. | 604/43 |
| 4,583,968 | 4/1986 | Mahurkar | 604/43 |
| 4,813,429 | 3/1989 | Eshel et al. | 604/43 |
| 4,902,276 | 2/1990 | Zakko | 604/43 |
| 4,995,865 | 2/1991 | Gahara et al. | 604/43 |
| 5,009,636 | 4/1991 | Wortley et al. | 604/280 |
| 5,041,083 | 8/1991 | Tsuchida et al. | 604/43 |

Primary Examiner—Paul J. Hirsch
Attorney, Agent, or Firm—Alvin Isaacs

[57] ABSTRACT

Disclosed is a dual lumen catheter for insertion within a blood vessel of a patient. The dual lumen catheter has an elongated flexible tube with three conduits contained therein. The first and second conduits are connected together by an opening in the common wall therebetween, which opening extends through the wall of the catheter tube. The third passageway forms a second lumen. Each of the lumens has means adapted for placement of the lumen in fluid communication with a source of liquid to be administered to the patient through the catheter, to means for withdrawing a blood sample or to means for monitoring blood pressure.

4 Claims, 2 Drawing Sheets

DUAL LUMEN CATHETER

BACKGROUND OF THE INVENTION

This invention relates to a dual lumen catheter for the purpose of infusing a plurality of fluids into a patient's blood vessel, wherein one of the lumens has a pair of passageways.

DESCRIPTION OF THE PRIOR ART

Prior catheter devices utilize a single lumen or multiple lumens with independent passageways. These passageways are used for such functions as drawing and returning blood simultaneously; to administer a drug; intravenous feeding; monitor blood pressure; or to take blood samples. It is generally considered undesirable to mix drugs or fluids prior to their entering the bloodstream. However many patients require simultaneous infusion of different medications or other fluids.

A primary object of the invention is to provide an improved dual lumen catheter for continuously and simultaneously drawing and returning blood to a patient, e.g. dialysis and plasmapheresis.

Accordingly, a further object of this invention is to provide an improved dual lumen catheter with which to infuse two fluids simultaneously into the vein of a patient.

Another object of the present invention is to provide an improved dual lumen catheter which may be used to monitor blood pressure simultaneously with fluid/drug infusion, and which may be used to withdraw blood samples.

Still another object is to provide a dual lumen catheter having less tendency for kinking.

Yet another object is to provide a more supple and pliable dual lumen catheter.

Other objects of the invention will be obvious in the light of the following detailed description of the invention.

SUMMARY OF THE INVENTION

According to the present invention, these objects are attained by providing a dual lumen catheter for simultaneous infusing of fluids into and/or withdrawing blood from a patient's blood vessel wherein the catheter tube has three longitudinally extending conduits. One of the conduits forms a lumen terminating in an opening or port at its distal end. The second and third conduits form another lumen (which may be termed a "co-lumen") in which the second and third conduits connect with a common lateral side opening or port that also spans the interior of their common support wall. The second and third conduits are common at both their distal and proximal ends and the common support wall which separates the second and third conduits of the second or co-lumen reduces the tendency of the catheter tube to kink while at the same time providing a more supple and pliable catheter tube.

The novel features as well as the nature and objects of the invention, both as to organization and method of operation, will best be understood from the following detailed description taken in conjunction with the accompanying illustrative drawings.

DETAILED DESCRIPTION OF THE INVENTION

Figure 1:
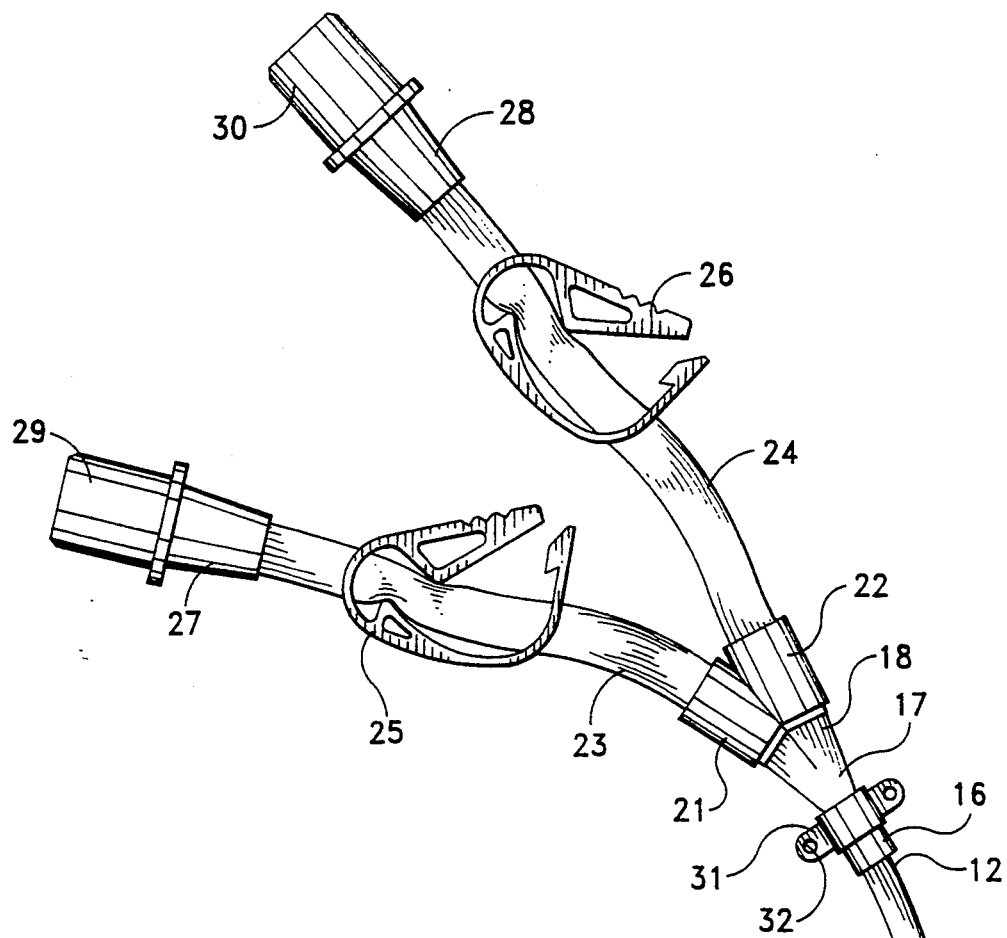
FIG. 1 is a schematic side view of the dual lumen catheter of the present invention.

Referring to FIG. 1, there is shown the preferred embodiment of the dual lumen catheter of this invention, generally designated as 1. The dual lumen catheter 1 has an elongated, flexible catheter tube 10 with a tapered distal end 11 capable of insertion into and being fed longitudinally within a blood vessel of a patient.

Those skilled in the art will appreciate that the tapered distal end 11 is conventionally introduced over a guide wire which has previously been placed within the blood vessel. Those skilled in the art will also understand that the common method to accomplish the placement of the guide wire within a blood vessel is the well-known "Seldinger Technique". After penetration by the needle and insertion of the guidewire into the blood vessel, the catheter tube 10 is then fed longitudinally over the guidewire for a sufficient length so as to introduce within the blood vessel the lateral side ports 13, 14, 15 opening to the interior of the catheter tube 10. The tube 10 is connected at its proximal end 12 to the distal end 16 of a fluid-conveying hollow hub assembly 17. Hub assembly 17 is divided or splits at its proximal end 18 into two hub segments 21, 22 which are connected to tubing extensions 23, 24 respectively. The tubing extensions 23, 24 are in turn connected at their proximal ends to adapters 27, 28 respectively for attachment to a suitable device or fluid source. As shown in FIG. 1, adapters 27, 28 are provided with luer-lock caps 29, 30 respectively, for covering the adapters when they are not in use connecting the tubing extensions. Also as shown in FIG. 1, conventional clamps 25, 26 are provided to open and close tubing extensions 23, 24 respectively, as desired.

While not necessary to the practice of the invention, suture tab 31 having a pair of holes 32 is preferably provided for securing the catheter to the patient by means of a suture.

Figure 2:
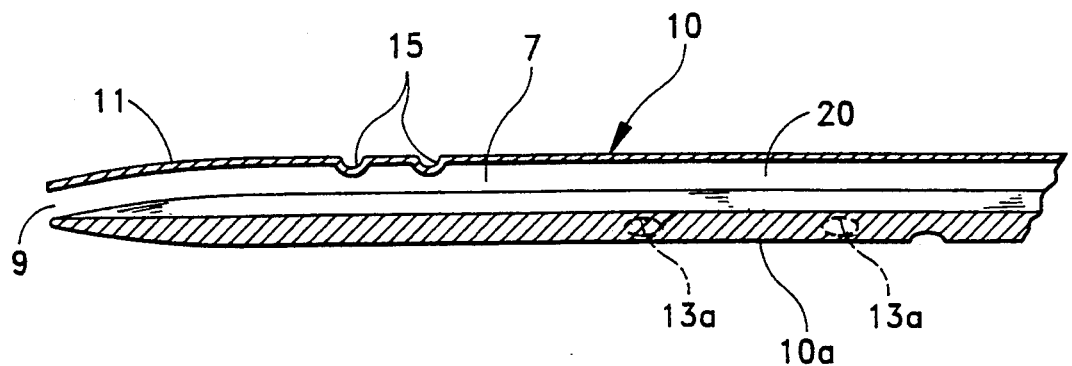
FIG. 2 is a side section view of the invention along Line 2—2' of FIG. 1.
Figure 3:
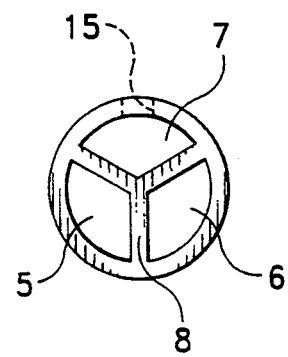
FIG. 3 is a cross-sectional view of the catheter tube of FIG. 1.
Figure 4:
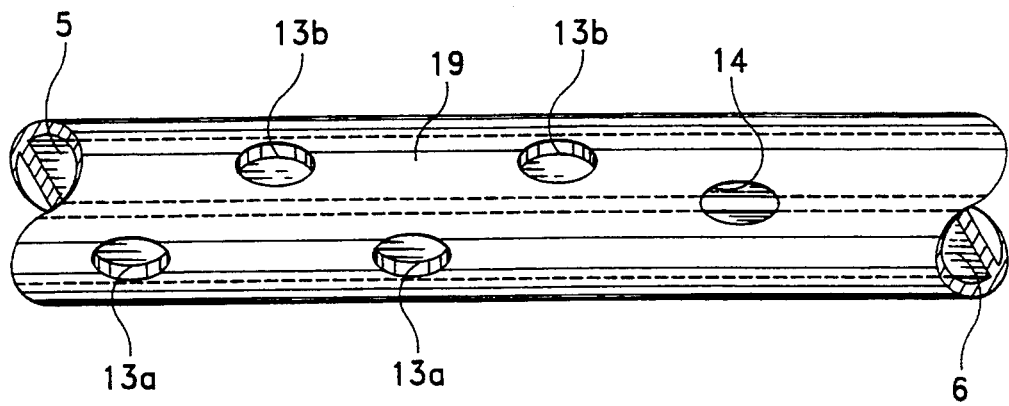
FIG. 4 is a bottom plan view of a portion of the catheter of FIG. 1, partially broken away.

Referring now to FIGS. 2-4, there is shown to be three longitudinally extending conduits 5, 6 and 7 within the catheter tube 10. FIG. 3 shows the generally circular crosssection of the catheter tube 10 with the three conduits 5, 6 and 7 contained therein.

The cross-sectional appearance is of a trilocular configuration (which one will observe resembles the logo of a Mercedes-Benz automobile) trifurcating the lumens into three conduits. As seen, a novel feature of this invention is that the conduits 5, 6 cooperate to form a first or co-lumen 19; while conduit 7 forms a second lumen 20. In the preferred embodiment, the combined cross-sectional area of the conduits 5, 6 of the first lumen is substantially equal to the cross-sectional area of conduit 7 of the second lumen. However, where found desirable to do so, it is contemplated that the cross-sectional area of conduits 5,6 may be greater or less than that of conduit 7.

The common wall or septum 8 of conduits 5, 6 is perforated to provide a port 14 which extends laterally through the wall 10a of the catheter tube 10. This hole enables the fluid in conduits 5/6 to infuse into the blood stream of the patient. In addition, two lateral side ports 13a and 13b are separately spaced in the side wall of conduits 5 and 6, respectively. These lateral side ports 13a and 13b enable entry and discharge of fluid from the individual conduits 5, 6 within first lumen 19. The conduit 7 of second lumen 20 has an end port 9 at its distal end. It is also provided with two side ports 15 which are spaced apart near the distal end 11 of the catheter. Fluids may be infused or blood withdrawn efficiently through the second lumen 20 through the end port 9 and side ports 15 of conduit 7.

In accordance with the present invention, the dual lumens 19, 20 are totally independent and non-communicative with one another so that fluid carried therein will not mix prior to entering the bloodstream. However, as mentioned, passageways 5,6 are communicative with one another through common side port 14 so that fluid from both of the co-conduits 5, 6 may be introduced into the bloodstream through common port 14.

Depending on the source to which the tube extensions 23 and 24 are in communication, the dual lumen catheter of this invention may also be employed in per se known manner to continuously draw and return blood to a patient, monitor blood pressure and/or obtain a blood sample and/or infuse fluid into the blood vessel of the patient.

In use, a guidewire is first introduced into the desired blood vessel in the direction of the flow of blood, e.g. by the aforementioned "Seldinger Technique." Thereafter, the distal end 11 of the catheter tube 10 is fed into the puncture over the guide wire the desired distance until all the ports 13, 14, 15 are fully within the blood vessel. The luer-lock caps 29, 30 are removed and the catheter tube 10 placed in fluid communication via extension tubings 23, 24 with the desired device and/or fluid source for administration to the patient. As is well understood, when drug syringes are employed, for example, the drugs are injected into adapters 27, 28 where they then flow through extension tubings 23, 24 and then through hub assembly 17 into the dual lumens 19, 20 respectively for introduction within the blood vessel through the distal portion of the catheter tube.

From the foregoing description it will thus be seen that the present invention provides a novel dual lumen catheter satisfying the objectives of the invention. The task of inhibiting kinking is solved by the septum 8 splitting one of the lumens into two conduits.

It will be appreciated that various changes may be made without departing from the scope of the invention herein contemplated. For example, while for purposes of illustration the invention has been described with reverence to two ports 13a, 13b and 14, respectively in each of the conduits 5, 6 and 7, it is contemplated that a lesser or greater amount of ports may be utilized in each of the conduits, i.e. each may have but a single port or a plurality of ports greater than the two shown in the drawings.

It is also contemplated that if desired, conduit 7 may also be separated into two conduits by means of a septum similar to septum 8 in lumen 19. In the illustrative drawings, conduits 5 and 6 are shown to be substantially equal in cross-sectional area. While this is preferred, it is not necessary however, to the practice of this invention.

Accordingly, it is to be expressly understood that the foregoing description and accompanying drawings are merely illustrative of the preferred embodiment of the dual lumen catheter of the present invention, and that no limitations are intended other than as defined in the appended claims.

What is claimed is:

1. A dual lumen catheter comprising:
   an elongated flexible catheter tube having a generally circular cross-section;
   the catheter having an outer wall member having a proximal end and an opposed distal end terminating in a tip for insertion within a patient's blood vessel;
   the catheter having inner wall members trifurcating the catheter tube into a first, a second and a third longitudinally extending conduit, the inner wall members consisting of a first wall member common to and separating the first and second conduits, a second wall member common to and separating the first and third conduits, and a third wall member common to and separating the second and third conduits;
   the common wall member separating the first and second conduits being perforated to provide a side port which extends laterally through the outer wall of the catheter tube in the distal end section of the catheter, the first and second conduits thereby forming a first lumen wherein fluid introduced into the first and second conduits through the proximal end of the catheter can together infuse into the blood vessel where the catheter has been introduced through the side port; and
   the third conduit defined by the outer wall and the second and third inner wall members forming a second lumen having an end port at the tip of the catheter.

2. A dual lumen catheter as defined in claim 1 wherein the first lumen is in fluid communication with a source of liquid to be introduced into the blood vessel.

3. A dual lumen catheter as defined in claim 1 wherein the combined cross-sectional area of the first and second conduits forming the first lumen is substantially equal to the cross-sectional area of the second lumen.

4. A dual lumen catheter as defined in claim 1 wherein each of the first and second conduits forming the first lumen additionally has at least one side port in the distal end section to be inserted in the patient's blood vessel, the additional side ports being separately spaced in the outer wall.

* * * * *